US006271199B2

(12) United States Patent
Brand et al.

(10) Patent No.: US 6,271,199 B2
(45) Date of Patent: Aug. 7, 2001

(54) TREATMENT OF INFARCTS

(75) Inventors: Stephen J Brand, San Diego, CA (US); Alfred L. Goldberg, Chestnut Hill, MA (US); Louis Plamondon, Watertown, MA (US); Francois Soucy, Arlington, MA (US); Peter J. Elliott, Marlborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/285,170

(22) Filed: Nov. 24, 1998

Related U.S. Application Data

(63) Continuation-in-part of application No. 08/988,339, filed on Dec. 3, 1997, now abandoned, which is a continuation-in-part of application No. 08/801,936, filed on Feb. 15, 1997, now abandoned.

(51) Int. Cl.[7] .................. A61K 38/00; A61K 31/495; A61K 31/40
(52) U.S. Cl. ...................... 514/2; 514/252.1; 514/421
(58) Field of Search ................. 514/2, 252.1, 421

(56) References Cited

U.S. PATENT DOCUMENTS

| | | | |
|---|---|---|---|
| 5,942,494 | 8/1999 | Ginsberg et al. | 514/18 |
| 6,133,308 | 10/2000 | Soucy et al. | 514/423 |

FOREIGN PATENT DOCUMENTS

| | | |
|---|---|---|
| 91/13904 | 9/1991 | (WO) . |
| 95/24914 | 9/1995 | (WO) . |
| 95/25533 | 9/1995 | (WO) . |
| 96/13266 | 5/1996 | (WO) . |
| 96/32105 | 10/1996 | (WO) . |
| 96/35430 | 11/1996 | (WO) . |
| 97/35014 | 9/1997 | (WO) . |

OTHER PUBLICATIONS

U.S. Application No. 09/642,275, (Goldberg et al.) Aug. 18, 2000.
U.S. application No. 08/832.301 (Goldberg et al.) Apr. 3, 1997.
U.S. Application Serial No. 08/832,301 filed Apr. 9, 1997 by Goldberg et al., now abandoned.
Alkalay et al.: Stimulation–dependent IκΑ phosphorylation marks the NF–κB inhibitor for degradation via the ubiquitin–proteasome pathway; (1995); Proceedings of the National Academy of Sciences; 92: pp. 10559–10603.

Chen et al.: Site–Specific Phosphorylation of IκBαby a Novel Ubiquitination–Dependent Protein Kinase Activity; (1996); *Cell*: 84: pp. 853–862.
Berleth et al.: Mechanism of Ubiquitin Conjugating Enzyme E2–230K: Catalysis Involving a Thiol Relay; (1966); *Biochemistry*; 35: pp. 1664–1671.
Koong et al.: Hypoxia Causes the Activation of Nuclear Factor κB through the Phosphorylation of IκBα on Tyrosine Residues[1]; (1994); *Cancer Research*; 54: pp. 1425–1430.
Baldwin: The NF–κB and IκB Proteins: New Discoveries and Insights; (1996); *Annu. Rev. Immunol*; 14: pp. 649–681.
Barnes et al.: Nuclear Factor–κB—A Pivotal Transcription Factor in Chronic Inflammatory Diseases; (1997); *The New England Journal of Medicine*; 336:15: pp. 1066–1071.
Manning et al.: Transcription Factor NF–κB: An Emerging Regulator of Inflammation; (1994); Annual Reports in Medicinal Chemistry; 29: pp. 235–244.
Grilli et al.: NF–κB and Rel: Participants in a Multiform Transcriptional Regulatory System; (1993); *Cytology*; 143: pp. 1–62.
Read et al.: The Proteasome Pathway is Required for Cytokine–Induced Endothelial–Leukocyte Adhesion Molecule Expression; (1995); *Immunology*; 2: pp. 493–506.
Werns: Free Radical Scavengers and Leukocyte Inhibitors; .*Textbook of Interventional Cardiology*, (1994); pp. 142–153.
Forman et al.: Pathogenesis and Modification of Myocardial Reperfusion Injury; (1991); *Acute Myocardial Infarction*: pp. 347–370.
Collins: Biology of Disease, Endothelial Nuclear Factor–κB and The Initiation of the Atherosclerotic Lesion; (1993); *Laboratory Investigation*; 68 (5): pp. 499–508.
Traenckner et al.: A Proteasome Inhibitor Prevents Activation of NF–κB and Stabilizes a Newly Phosphorylated Form of IκBα That is Still Bound to NF–κB; 1994; *The EMBO Journal*; 13 (22): pp. 5433–5441.
Iqbal et al.: Protein Inhibitors of Proteasome; (1995); *J. Med. Chem.*; 38: pp. 2276–2277.
Fenteany et al.: A β–lactone Related to Lactacystin Induces Neurite Outgrowth in a Neuroblastoma Cell Line and Inhibits Cell Cycle Progression in an Osteosarcoma Cell Line; (1994); *Biochemistry*; 91: pp. 3358–3362.

*Primary Examiner*—Raymond Henley, III
(74) *Attorney, Agent, or Firm*—Hale and Dorr LLP

(57) ABSTRACT

This invention is directed to treating ischemia by administering proteasome inhibitors, ubiquitin pathway inhibitors, agents that interfere with the activation of NF-κB via the ubiquitin proteasome pathway, or mixtures thereof.

24 Claims, 8 Drawing Sheets

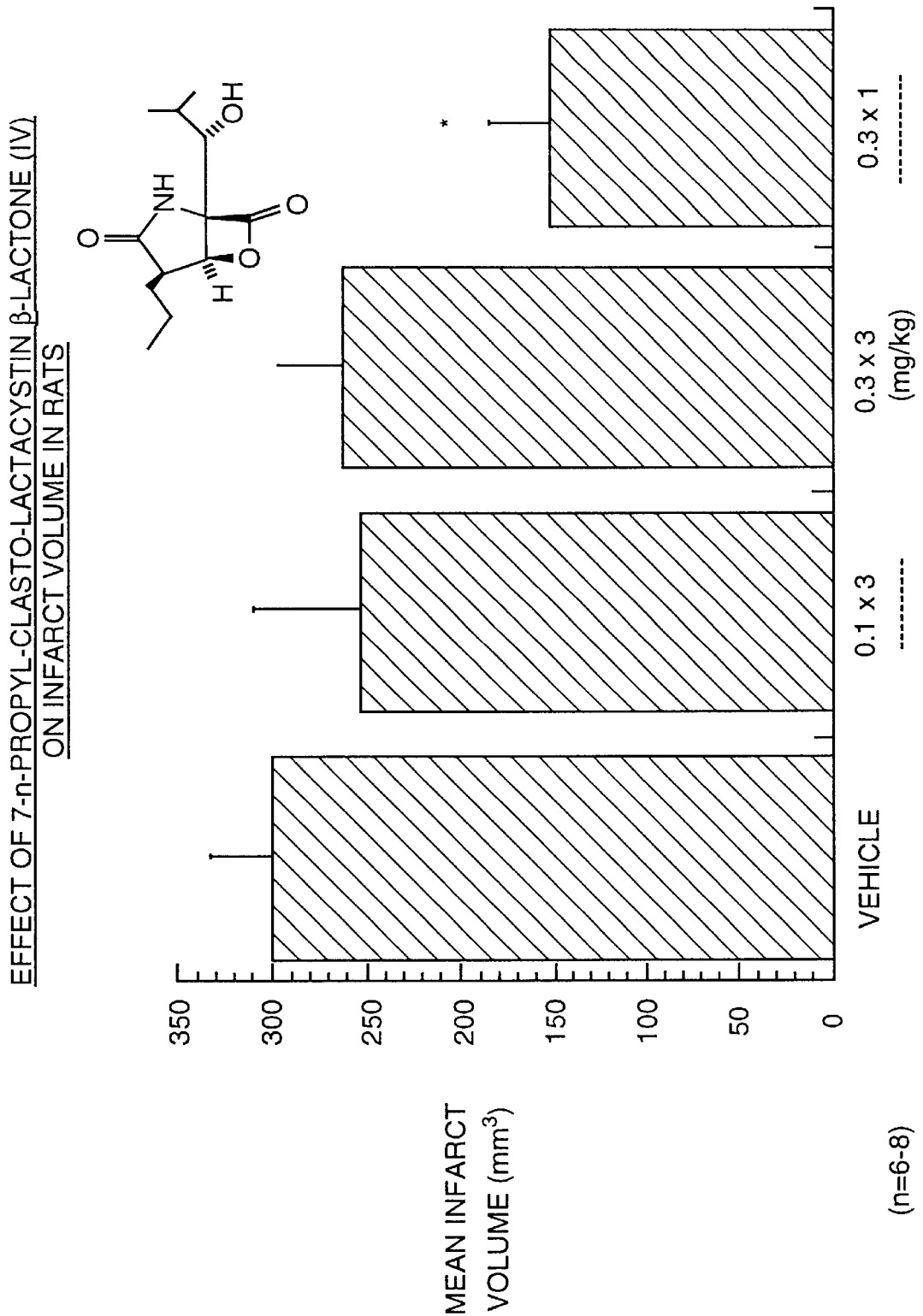

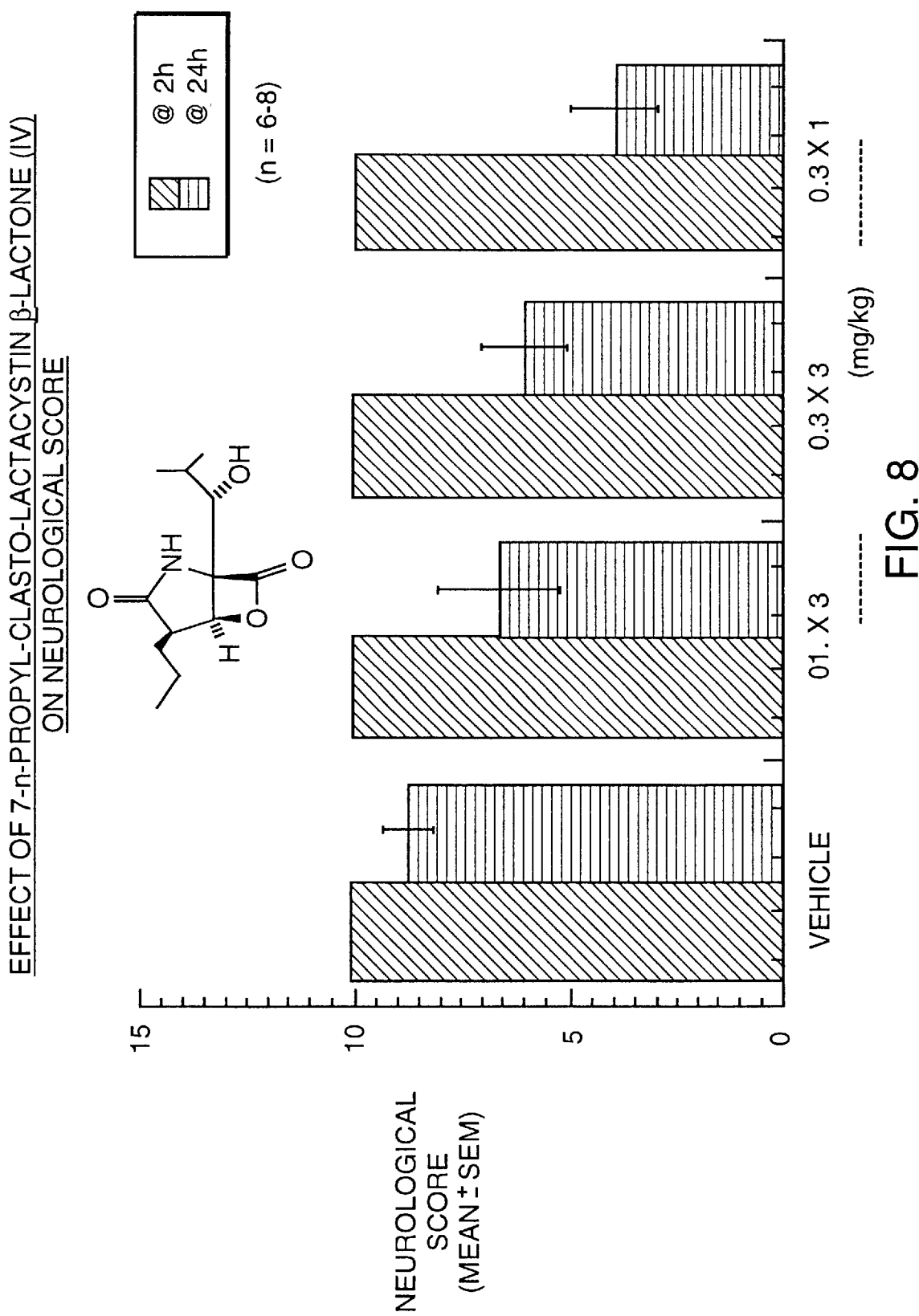

TREATMENT OF INFARCTS

CROSS-REFERENCE TO RELATED APPLICATIONS

This application is a continuation-in-part of U.S. application Ser. No. 08/988,339, filed Dec. 3, 1997, now abandoned, which is a continuation-in-part of U.S. application Ser. No. 08/801,936, filed Feb. 15, 1997, now abandoned.

FIELD OF THE INVENTION

This invention relates to treatment of ischemia and reperfusion injury, including preventing or reducing the size of infarct after vascular occlusion.

BACKGROUND OF THE INVENTION

All tissues are sensitive to hypoperfusion and the resulting lack of oxygen, ischemia. Prolonged ischemia will result in cellular damage. The magnitude of the injury and the potential for tissue rescue depends upon the degree and duration of the ischemia. With long ischemic periods, cellular death occurs (infarction) and under these conditions the injury is irreversible. On the other hand, dying cells or cells targeted for cell death may be rescued by drug treatment, if applied in a timely fashion.

Major ischemic events of therapeutic concern include, but are not limited to, heart attacks and stroke. In man, stroke accounts for 10% of all premature deaths, and of those that survive the insult, 50% are left severely disabled. Only a small fraction, 10%, of patients actually recover full function.

Over 1,500,000 Americans suffer from myocardial infarctions each year. About half of these do not survive to reach the hospital. However, with the acceptance of thrombolytic therapy such as streptokinase or tissue plasminogen activator (TPA), the one month survival rate for patients who do reach the hospital is as high as 93.6% (Werns, S. W. *Textbook of Interventional Cardiology*, ed. Topol, E. J. WB Saunders: 1994, pp142–153). By lysing the clot early in the course of infarct, ischemic muscle and tissue can be salvaged. However, reperfusion in and of itself leads to tissue damage.

Reperfusion injury may occur as a result of one or more of the following events: cellular acidosis leading to calcium overload; increased intracellular osmotic loads of catabolites leading to cell swelling; free radicals from neutrophils and other inflammatory cells.

Neutrophils are seen in reperfused myocardium shortly after reperfusion. Monocytes/macrophages appear within 24 to 48 hours. Neutrophil infiltration is three to five fold greater in reperfused myocardium than in ischemic myocardium, is initiated by adhesion to endothelial cells, and occurs within 10 minutes of reperfusion. Neutrophils in and of themselves may become trapped in capillaries and impede reperfusion. Intravascular neutrophils may block up to 27% of the capillaries, and have been shown to be related to decreased regional blood flow (Forman et al., *Acute Myocardial Infarction*, eds. Gersh et al. Elsevier: 1991, pp 347–370). This can result in the "no-reflow" phenomenon, where blood flow continues to decrease after reperfusion.

It is known that neutrophils must first adhere themselves to the endothelial cell wall through the interactions with adhesion molecules. Once attached to the vessel cell wall, the neutrophils then force themselves between adjacent endothelial cells and move into the brain tissue, where they release cytotoxic cytokines. The expression of such adhesion molecules is increased following cell damage including ischemia. In addition, endothelial cell walls become more permeable to infiltrating cells due to the release of nitric oxide (NO). Agents that inhibit the movement (diapedesis) of neutrophils from surrounding blood vessels into the damaged tissue may thus be of value in allowing dying cells time to recover from the ischemic insult.

There is a need in the art for effective therapies to prevent or reduce the consequences of ischemia.

SUMMARY OF THE INVENTION

In a first aspect, the present invention is directed to a method of treating ischemia in a mammal comprising administering to said mammal an effective amount of an NF-κB activation inhibitor. Preferred NF-κB activation inhibitors are selected from the group consisting of proteasome inhibitors, ubiquitin pathway inhibitors, inhibitors of serine phosphorylation of IκB-α. and mixtures thereof. Preferably, the agent is administered to the mammal after the onset of transient vascular occlusion and prior to induction of permanent ischemic damage.

In a second aspect, the present invention is directed to a method of preventing or lessening the severity reperfusion injury in a mammal comprising administering to said mammal an effective amount of an NF-κB activation inhibitor. Preferred NF-κB activation inhibitors are selected from the group consisting of proteasome inhibitors, ubiquitin pathway inhibitors, inhibitors of serine phosphorylation of IκB-α. and mixtures thereof.

In a third aspect, the present invention is directed to a method of preventing, reducing the size of, or lessening the severity of infarction in a mammal comprising administering to said mammal an effective amount of an NF-κB activation inhibitor. Preferred NF-κB activation inhibitors are selected from the group consisting of proteasome inhibitors, ubiquitin pathway inhibitors, inhibitors of serine phosphorylation of IκB-α. and mixtures thereof. In preferred embodiments, the method according to this aspect of the invention prevents or lessens severity of infarction after occlusion of a cerebral vessel or a cardiac vessel. In certain preferred embodiments, the method prevents the occlusion from resulting in stroke, or lessens the severity of a stroke resulting from cerebral vessel occlusion.

In a fourth aspect, the present invention is directed to a method of treating ischemia or reperfusion injury, including preventing or lessening the severity of infarction in a mammal comprising administering to the mammal an adjunct therapeutic, in addition to administering an NF-κB activation inhibitor. Preferred NF-κB activation inhibitors are selected from the group consisting of proteasome inhibitors, ubiquitin pathway inhibitors, inhibitors of serine phosphorylation of IκB-α. and mixtures thereof. Certain preferred adjunct therapeutics include without limitation, agents such as steroids which further inhibit NF-κB activation or inhibit the expression or action of proinflammatory cytokines or cellular adhesion molecules; agents which act to either reperfuse or oxygenate tissues, such antiedema drugs, thrombolytics such as TPA, streptokinase and urokinase, polyanions such as heparin, anticoagulants; and agents that assist in temperature normalization.

Preferred NF-κB activation inhibitors inhibit NF-κB activation by the ubiquitin-proteasome pathway. In certain preferred embodiments, the NF-κB activation inhibitor inhibits phosphorylation of IκB-α. In certain preferred embodiments, the NF-κB activation inhibitor is a proteasome inhibitor. Preferably, the proteasome inhibitor is selected from the group consisting of peptidyl aldehydes, boronic acids, boronic esters, lactacystin, and lactacystin analogs. In certain preferred embodiments, NF-κB activation inhibitor is a ubiquitin pathway inhibitor.

BRIEF DESCRIPTION OF THE DRAWINGS

FIG. 7 is directed to reduction of infarct volume by administration of the proteasome inhibitor 7-n-propyl-clasto-lactacystin β-lactone.

FIG. 8 is directed to reduction of neurological score by administration of the proteasome inhibitor 7-n-propyl-clasto-lactacystin β-lactone.

DETAILED DESCRIPTION OF THE INVENTION

Figure 1:
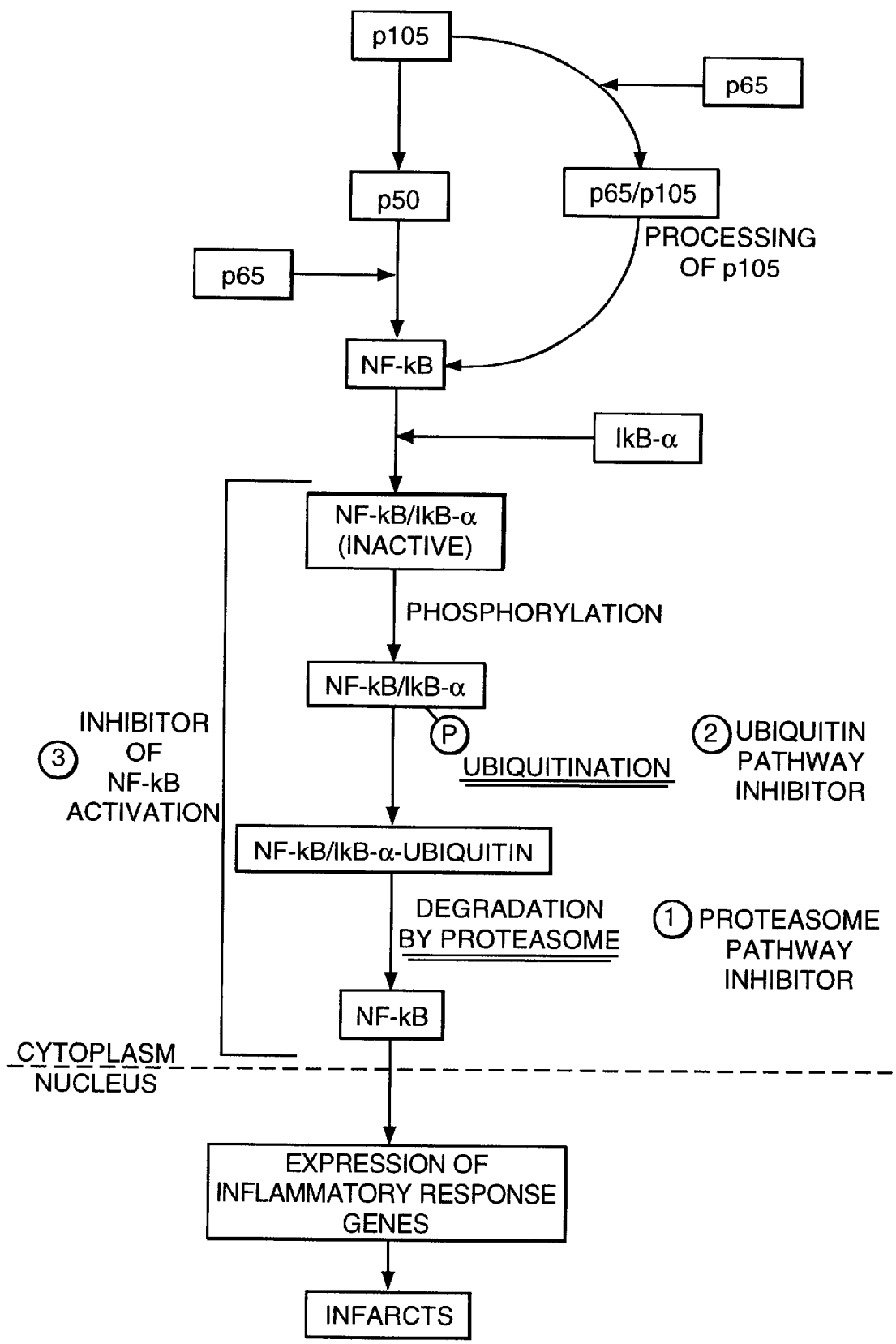
FIG. 1 shows the cascade of NF-κB activation leading to reperfusion injury, including infarct. Points of intervention by the methods according to the invention are indicated.

The invention relates to treatment of ischemia and reperfusion injury, including preventing, reducing the size or lessening the severity of infarct after vascular occlusion. The patent applications, patents and literature references cited herein indicate the knowledge in this field and are hereby incorporated by reference in their entirety. In the case of inconsistencies the present disclosure will prevail.

It has now been unexpectedly discovered that the ubiquitin-proteasome pathway is a target for treating ischemia and reperfusion injury, including preventing, reducing the size, or lessening the severity of infarcts following vascular occlusions such as occur during heart attack or stroke, and that inhibitors of NF-κB activation via the ubiquitin-proteasome pathway can provide effective therapy for these conditions. The invention provides surprisingly effective methods for treating ischemia or reperfusion injury.

The present inventors have discovered that blocking proteasome function reduces the effects of ischemia, such as reducing infarct size following vascular occlusion. This can be done by direct proteasome inhibition (shown with N-(2-pyrazine)carbonyl-L-phenylalanine-L-leucine boronic acid and 7-n-propyl-clasto-lactacystin β-lactone) or by blocking ubiquitination of proteasome-targeted proteins such as IκB-α. Any inhibitors which affect activation of NF-κB via the ubiquitin/proteasome pathway in eukaryotic cells are expected to be effective in preventing or treating infarction, including infarction following vascular occlusion and are thus in the scope of the present invention.

In accordance with the present invention, treatment of ischemia, including reperfusion injury, prevention of infarction and reduction in size or lessening of severity of infarct is achieved by administering to a mammal an effective amount of an NF-κB activation inhibitor. Preferred NF-κB activation inhibitors are selected from the group consisting of proteasome inhibitors, ubiquitin pathway inhibitors, inhibitors of serine phosphorylation of IκB-α, and mixtures thereof.

In a first aspect, the present invention is directed to a method of treating ischemia in a mammal comprising administering to said mammal an effective amount of an NF-κB activation inhibitor. All tissues are sensitive to lack of oxygen (ischemia) resulting from hypoperfusion. Major ischemic events of therapeutic concern include, but are not limited to, heart attacks and stroke. Ischemia also can affect other tissues, including retinal, liver, kidney, bone, placental and spinal tissue. Prolonged ischemia results in cellular damage, manifest, in the case of cerebral ischemia, as neurological dysfunction. Agents currently used in treatment of stroke are targeted at 1) reversing excessive excitotoxic phenomena associated with an ischenmic episode; or 2) increasing blood flow to ischermic tissue.

Ischemic injury may commonly result from e.g., vascular occlusion such as by an embolus or thrombus, hemorrhage, near drowning and near suffocation. Without wishing to be bound by theory, it is believed that ischemia causes a massive release of the excitotoxic amino acid, glutamate, from presynaptic nerve endings in the brain which act on N-methyl-D-aspartate (NMDA) receptors on adjacent cells. Once activated, NMDA receptors allow excessive calcium to enter the cell, which in turn activates a number of secondary pathways that ultimately lead to cellular protein degradation and cell death. In the search for effective therapies, efforts have been made to target either the release of presynaptic glutamate (via κ-opiate receptor stimulation), or blockade of NMDA receptor activation (either directly, with NMDA antagonists, or indirectly, with glycine antagonists). Calcium channel blockers and calpain inhibitors have also been investigated. While individual drugs have shown activity in both preclinical and clinical situations, the benefit is limited due to the speed at which the cascade occurs, the time taken for the drugs to be given, and the effectiveness of the therapy. The only drug used clinically to increase blood flow is tissue plasminogen activator (TPA), which aids in the rapid solubilization of clots that are responsible for the vessel blockade. While effective to a limited extent in stroke patients, by actually promoting bleeding, drugs like TPA can be lethal to those patients that have cerebral hemorrhage. As such, TPA cannot be given until the patient has been confirmed as having a stroke rather than hemorrhage. For a stroke patient, the time taken for this analysis to occur obviously increases the length of time of the ischemia and hence the amount of salvageable tissue is reduced. Agents such as NF-κB activation inhibitors that can act on the ischemic cascade system itself are not limited by such a prolonged diagnosis period, as they are not detrimental in cerebral hemorrhage patients.

Preferred NF-κB activation inhibitors inhibit NF-κB activation by the ubiquitin-proteasome pathway. In certain preferred embodiments, the NF-κB activation inhibitor inhibits phosphorylation of IκB-α. In certain preferred embodiments, the NF-κB activation inhibitor is a proteasome inhibitor. In such embodiments the inhibition of the proteasome is preferably less than complete inhibition. Preferably, the proteasome inhibitor is selected from the group consisting of peptidyl aldehydes, boronic acids, boronic esters, lactacystin, and lactacystin analogs. In certain preferred embodiments, the NF-κB activation inhibitor is a ubiquitin pathway inhibitor.

The transcription factor NF-κB is a member of the Rel protein family. The Rel family of transcriptional activator proteins can be divided into two groups. The first group requires proteolytic processing, and includes p105 and p100, which are processed to p50 and p52, respectively. The second group does not require proteolytic processing and includes p65 (Rel A), Rel (c-Rel), and Rel B. NF-κB comprises two subunits, p50 and an additional member of the Rel gene family, e.g., p65. Unprocessed p105 can also associate with p65 and other members of the Rel family. In most cells, the p50–p65 heterodimer is present in an inactive form in the cytoplasm, bound to IκB-α. The ternary complex can be activated by the dissociation and destruction of IκB-α, while the p65/p105 heterodimer can be activated by processing of p105.

The ubiquitin-proteasome pathway plays an essential role in the regulation of NF-κB activity, being responsible both for processing of p105 to p50 and for the degradation of the inhibitor protein IκB-α. (Palombella et al., WO95/25533) In order to be targeted for degradation by the proteasome, IκB-α must first undergo selective phosphorylation at serine residues 32 and 36, followed by ubiquitination. (Alkalay et al., Proc. Natl. Acad. Sci. USA 92: 10599 (1995); Chen, WO97/35014)

Once activated, NF-κB translocates to the nucleus, where it plays a central role in the regulation of a remarkably diverse set of genes involved in the immune and inflammatory responses (Grilli et al, *International Review of Cytology* 143:1–62 (1993)). For example, NF-κB is required for the expression of a number of genes involved in the inflammatory response, such as TNF-α gene and genes encoding the cell adhesion molecules E-selectin, P-selectin, ICAM, and VCAM (Collins, T., *Lab. Invest.* (1993) 68:499. NF-κB is also required for the expression of a large number of cytokine genes such as IL-2, IL-6, granulocyte colony stimulating factor, and IFN-β. Inducible nitric oxide synthetase is also under regulatory control of NF-κB.

Proteasome inhibitors block IκB-α degradation and activation of NF-κB (Palombella et al. WO 95/25533 published Sep. 28, 1995; Traenckner, et al., *EMBO J.* (1994) 13:5433). Proteasome inhibitors also block TNF-α induced expression of the leukocyte adhesion molecules E-selectin, VCAM-1, and ICAM-1 (Read, et al., *Immunity* (1995) 2:493). These cell adhesion molecules play a critical role in supporting the emigration of leukocytes from the bloodstream to extravascular sites of injury such as ischemic tissue. Although intended to serve a repair function, the resultant influx of cells, particularly neutrophils, can promote damage by release of cytokines that speed cell death and signal additional cells (e.g., macrophages) to invade the area.

In a second aspect, the present invention is directed to a method of preventing or lessening the severity of reperfusion injury in a mammal comprising administering to said mammal an effective amount of an NF-κB activation inhibitor. Reperfusion injury may occur as a result of one or more of the following events: cellular acidosis leading to calcium overload; increased intracellular osmotic loads of catabolites leading to cell swelling; free radicals from neutrophils and other inflammatory cells. Preferred NF-κB activation inhibitors are selected from the group consisting of proteasome inhibitors, ubiquitin pathway inhibitors, inhibitors of serine phosphorylation of IκB-α. and mixtures thereof.

In a third aspect, the present invention is directed to a method of preventing, reducing the size of, or lessening the severity of infarction in a mammal comprising administering to said mammal an effective amount of an NF-κB activation inhibitor. Preferred NF-κB activation inhibitors are selected from the group consisting of proteasome inhibitors, ubiquitin pathway inhibitors, inhibitors of serine phosphorylation of IκB-α. and mixtures thereof. In preferred embodiments, the method according to this aspect of the invention prevents, reduces the size or lessens the severity of infarction after occlusion of a cerebral vessel or a cardiac vessel. In certain preferred embodiments, the method prevents the occlusion from resulting in stroke, or lessens the severity of a stroke resulting from cerebral vessel occlusion.

The most common form of stroke is thrombotic stroke, where occlusion of cerebral blood vessels is believed to be caused by a plug of aggregated platelets. Often, these platelet plugs are released as emboli from platelet thrombi on atherosclerotic plaques in major carotid or cerebral vessels. Thrombotic strokes often have a characteristic "stuttering" onset in which an initial modest, often reversible, neurological deficit is followed by a more severe, irreversible stroke. The initial event often reflects transient cerebrovascular obstruction by platelet thrombi, which is potentially reversible. Indeed, clinically, a mild stroke can be viewed as the extreme end of the spectrum of transient ischemic attacks (TIA)—a reversible neurological deficit in which a cerebral vessel is transiently occluded by an embolic platelet thrombus, which subsequently disaggregates, thus allowing flow to be reestablished. Therefore, the administration of an agent as disclosed herein after the onset of transient vascular occlusion is contemplated by the present invention. Another important form of stroke is stroke after cerebral hemmorhage, as discussed above. It is believed that the agents disclosed herein will have broad range efficacy in preventing, reducing the size, or lessening the severity of infarcts resulting from a variety of causes, including thrombotic stroke and stroke following cerebral hemmorhage. As a practical matter, the reduction of infarct size or lessening of infarct severity will be inferred from a reduction in symptoms associated with the infarct, including without limitation neurological symptoms and cardiac performance symptoms.

In a fourth aspect, the present invention is directed to a method to treating ischemia or reperfusion injury, including without limitation reducing the size or lessening the severity of infarction in a mammal comprising administering to the mammal an adjunct therapeutic, in addition to administering an NF-κB activation inhibitor. Preferred NF-κB activation inhibitors are selected from the group consisting of proteasome inhibitors, ubiquitin pathway inhibitors, inhibitors of serine phosphorylation of IκB-α. and mixtures thereof. Certain preferred adjunct therapeutics include without limitation, agents which such as steroids which further inhibit NF-κB activation or inhibit the expression or action of proinflammatory cytokines or cellular adhesion molecules; agents which act to either reperfuse or oxygenate tissues, antiedema drugs, thrombolytics such as TPA, streptokinase and urokinase, polyanions such as heparin, anticoagulants; and agents that assist in temperature normalization. Agents that inhibit the action of cytokines or cellular adhesion molecules include, without limitation, antibodies, or an antibody derivative, which may more preferably be a monoclonal antibody, a human antibody, a humanized antibody, a single-chain antibody, a chimeric antibody, or an antigen-binding antibody fragment. The use of any of the agents discussed or disclosed herein in combination with any other agent or agents used in the treatment of stroke or myocardial infarction is further contemplated within the scope of the present invention.

In the present description, the following definitions will be used.

"Treatment" shall mean preventing or lessening ischemic injury or reperfusion injury, including the prevention of infarction or reduction in size or lessening in severity of infarct, including without limitation infarct after vascular occlusion. Any amelioration of any symptom of the infarct pursuant to treatment using any proteasome inhibitor, ubiquitin pathway inhibitor, or agent that interferes with activation of NF-κB via the ubiquitin proteasome pathway is within the scope of the invention.

The term "mammals" is intended to include humans.

"Inhibitors of NF-κB activation" or "NF-κB activation inhibitors" shall mean any substance which inhibits of NF-κB activation via the ubiquitin proteasome pathway, and shall include any substance that 1) inhibits the proteasome or the activity thereof; 2) inhibits ubiquitination of IκB-α or p105; or 3) inhibits phosphorylation of IκB-α or p105.

"Ubiquitin pathway inhibitor" shall mean any substance which directly or indirectly inhibits ubiquitination or the transfer of ubiquitin to proteins. Non-limiting examples of ubiquitin pathway inhibitors include those disclosed in Berleth et al, *Biochem.* 35(5):1664–1671, (1996). Inhibitors of IκB-α phosphorylation are also known (Chen, *Cell* 84:853 (1996)).

"Proteasome inhibitor" shall mean any substance which directly or indirectly inhibits the proteasome or the activity thereof. Non-limiting examples of proteasome inhibitors for use in the present invention include peptide aldehydes (Stein et al. WO 95/24914 published Sep. 21, 1995; Siman et al. WO 91/13904 published Sep. 19, 1991; Iqbal et al. *J. Med. Chem.* 38:2276–2277 (1995)), peptide boronic acids (Adams et al. WO 96/13266 published May 9, 1996; Siman et al. WO 91/13904), lactacystin, and lactacystin analogs (Fenteany et al. *Proc. Natl. Acad. Sci. USA* (1994) 91:3358; Fenteany et al. WO 96/32105, published Oct. 17, 1996).

Peptide aldehyde proteasome inhibitors for use in the present invention preferably are those disclosed in Stein et al. WO 95/24914 published Sep. 21, 1995 or Siman et al. WO 91/13904 published Sep. 19, 1991, both hereby incorporated by reference in their entirety.

Boronic acid or ester compounds for use in the present invention preferably are those disclosed in Adams et al. WO 96/13266 published May 9, 1996, or Siman et al. WO 91/13904, both of which are hereby incorporated by reference in their entirety.

More preferably, the boronic acid compound for use in the present invention is selected from the group consisting of:

N-(4-morpholine)carbonyl-β-(1-naphthyl)-L-alanine-L-leucine boronic acid

N-(8-quinoline)sulfonyl-β-(1-naphthyl)-L-alanine-L-alanine-L-leucine boronic acid, N-(2-pyrazine)carbonyl-L-phenylalanine-L-leucine boronic acid, and N-(4-morpholine)carbonyl-[O-(2-pyridylmethyl)]-L-tyrosine-L-leucine boronic acid.

Lactacystin and lactacystin analog compounds for use in the present invention preferably are those disclosed in Fenteany et al. WO 96/32105, published Oct. 17, 1996, hereby incorporated by reference in its entirety. More preferably, the lactacystin analog is selected from lactacystin, clasto-lactacystin βlactone, 7-ethyl-clasto-lactacystin β-lactone and 7-n-propyl-clasto-lactacystin β-lactone are used for the methods of the invention. Most preferably the lactacystin analog is 7-n-propyl-clasto-lactacystin β-lactone.

The agents disclosed herein may be administered by any route, including intradermally, subcutaneously, orally, intraarterially or intravenously. Preferably, administration will be by the intravenous route. Preferably parenteral administration may be provided in a bolus or by infusion.

The concentration of a disclosed compound in a pharmaceutically acceptable mixture will vary depending on several factors, including the dosage of the compound to be administered, the pharmacokinetic characteristics of the compound(s) employed, and the route of administration. Effective amounts of agents for treating ischemia or reperfusion injury would broadly range between about 10 μg and about 50 mg per Kg of body weight of a recipient mammal. The agent may be administered in a single dose or in repeat doses. Treatments may be administered daily or more frequently depending upon a number of factors, including the overall health of a patient, and the formulation and route of administration of the selected compound(s).

The disclosed compound may be administered at any time before, during, or after the onset of ischemia. In certain preferred embodiments, the agent is administered after the onset of ischemia, but at a time early enough to reverse damage to some or all of the affected tissue. Preferably, the agent is administered less than 12 hours, more preferably less than 6 hours and still more preferably less than about 3 hours after onset of the ischemic event. Treatment may be initiated before, during or after reperfusion of the ischemic tissue. In many instances, the time of reperfusion cannot be accurately determined, but it is preferred that treatment begin before, during or soon after reperfusion to prevent or lessen additional damaging consequences which may result from reperfusion.

In the event of a clot inducing an ischemic episode, drugs such as TPA which break up the clot can be administered to reduce the potential tissue damage. Once dosed, the drug acts quickly to remove the vascular blockade and, therefore, the time at which the ischemic event ends can be determined. In one preferred embodiment, the inhibitor of NF-κB activation is administered at the same time or immediately following the clot dissolving drug.

In certain other preferred embodiments, the inhibitor of NF-κB activation is administered prior to the onset of ischemia. The onset of ischemia can be predicted in the case of certain medical procedures, such as surgical procedures. In another preferred embodiment, the disclosed compound is administered just prior to or immediately following the release of ischemia and onset of reperfusion during such a medical procedure (e.g., angioplasty procedures).

The following examples are intended to further illustrate certain preferred embodiments of the invention and are not limiting in nature.

EXAMPLES

Example 1

Methods

Six male Sprague Dawley rats (300 g) were anesthetized with haloethane and subjected to middle cerebral artery (MCA) occlusion using a nylon filament for 2 h. Subsequently, the filament was removed and reperfusion of the infarcted tissue occurred for 24 hours before the rat was sacrificed.

Staining of coronal sections (2.0 mm×7–8) with triphenyltetrazolium chloride (TTC) taken throughout the brain were evaluated under blinded conditions using image analysis to determine infarct size.

The infarct was also expressed as a percentage of the contralateral (non-infarcted) hemisphere to provide an indication of how much of the ipsilateral (infarcted) hemisphere was actually damaged by the procedure. Because edema is present in the infarcted hemisphere, it is often impossible to directly ascertain the percentage of the ipsilateral hemisphere that has been damaged.

Dosing Regimen

Rats were given iv bolus injections (1.0 mL/kg) of either vehicle (10% PEG 200/saline; n=3) or N-(2-pyrazine) carbonyl-L-phenylalanine-L-leucine boronic acid (0.03 mg/kg; n=3) at 30 minutes, 2 hours, and 6 hours after the start of the occlusion.

Results

Figure 2:
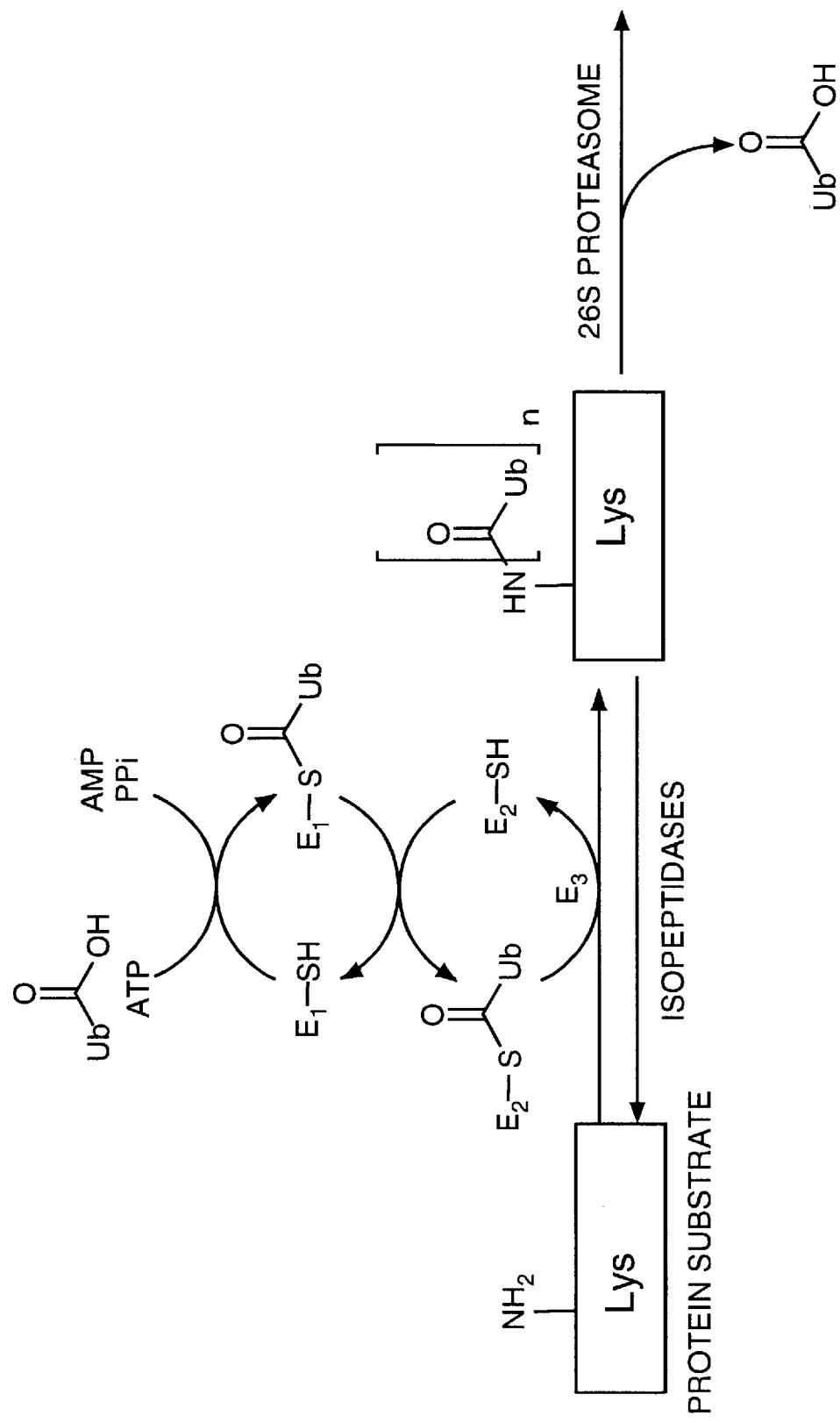
FIG. 2 shows the ubiquitin-proteasome pathway.

Infarct volume was decreased by 62% on the ipsilateral hemisphere in treated animals (FIG. 1). This reflects a decrease in total damage of the hemisphere from 19% to 2% (FIG. 2).

Example 2

Methods

Male Sprague Dawley rats (250–400 g) were anesthetized with haloethane and subjected to middle cerebral artery (MCA) occlusion using a nylon filament for 2 h. Subsequently, the filament was removed and reperfusion of the infarcted tissue occurred for 24 hours before the rat was sacrificed.

Immediately after the filament was withdrawn, the animals were evaluated using a neurological scoring system. Neurological scores were expressed on a scale from 0 to 10, with 0 representing no neurological deficit and 10 representing severe neurological deficit. After 24 hours and before sacrifice, animals were evaluated a second time using the same neurological scoring system.

Staining of coronal sections (2.0 mm ×7–8) with triphenyltetrazolium chloride (TIC) taken throughout the brain were evaluated under blinded conditions using image analysis to determine infarct size.

Dosing Regimen

Rats were given iv bolus injections (1.0 mL/kg) of either vehicle (50% propylene glycol/saline; n=8) or 7-n-propyl-clasto-lactacystin β-lactone (0.1 mg/kg; n=6) at 2 hours after the start of the occlusion.

Results

Figure 5:
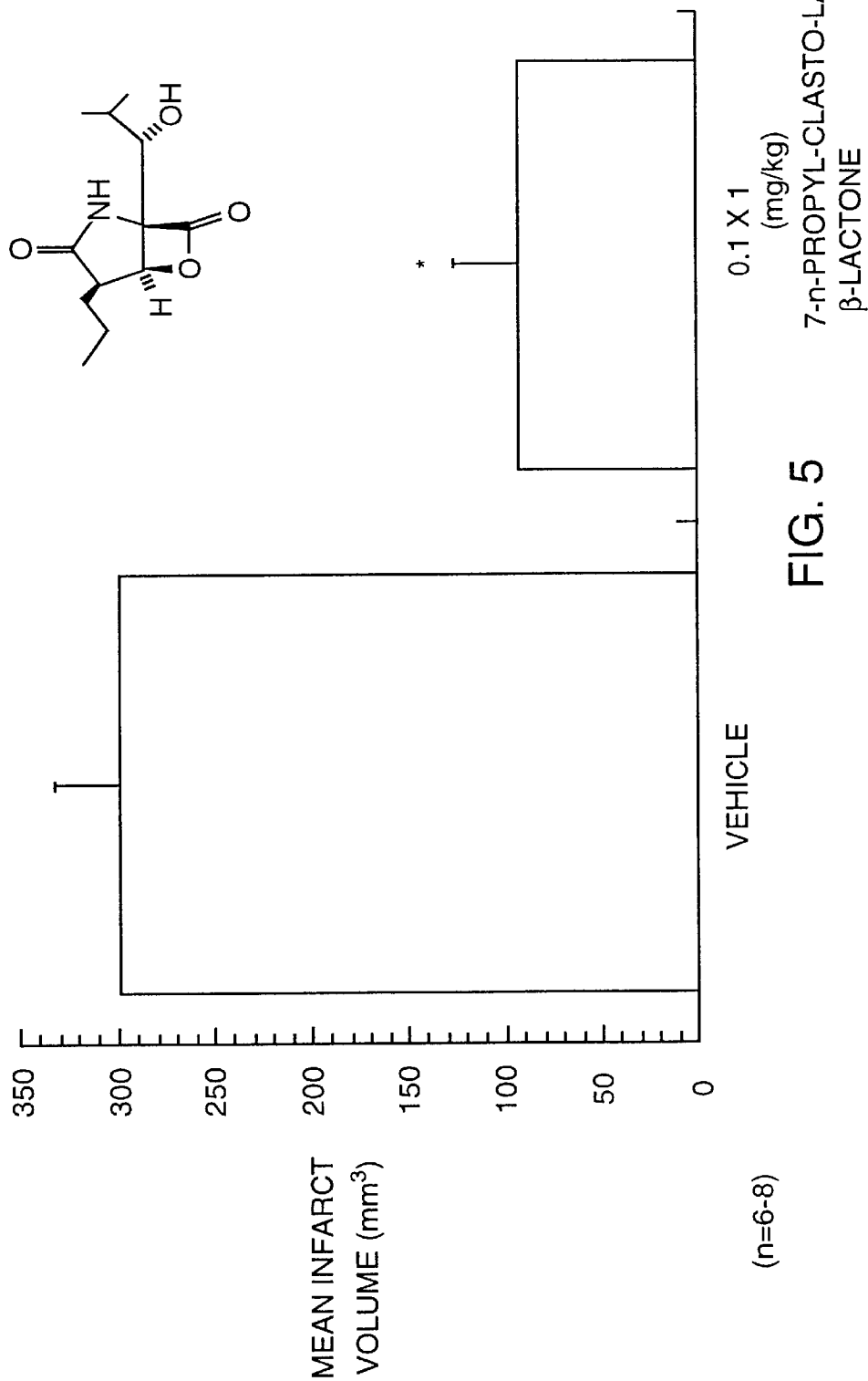
FIG. 5 is directed to reduction of infarct volume by administration of the proteasome inhibitor 7-n-propyl-clasto-lactacystin β-lactone following middle cerebral artery (MCA) occlusion.

In animals treated with 7-n-propyl-clasto-lactacystin β-lactone, infarct volume was decreased by 70% (FIG. 5).

Figure 6:
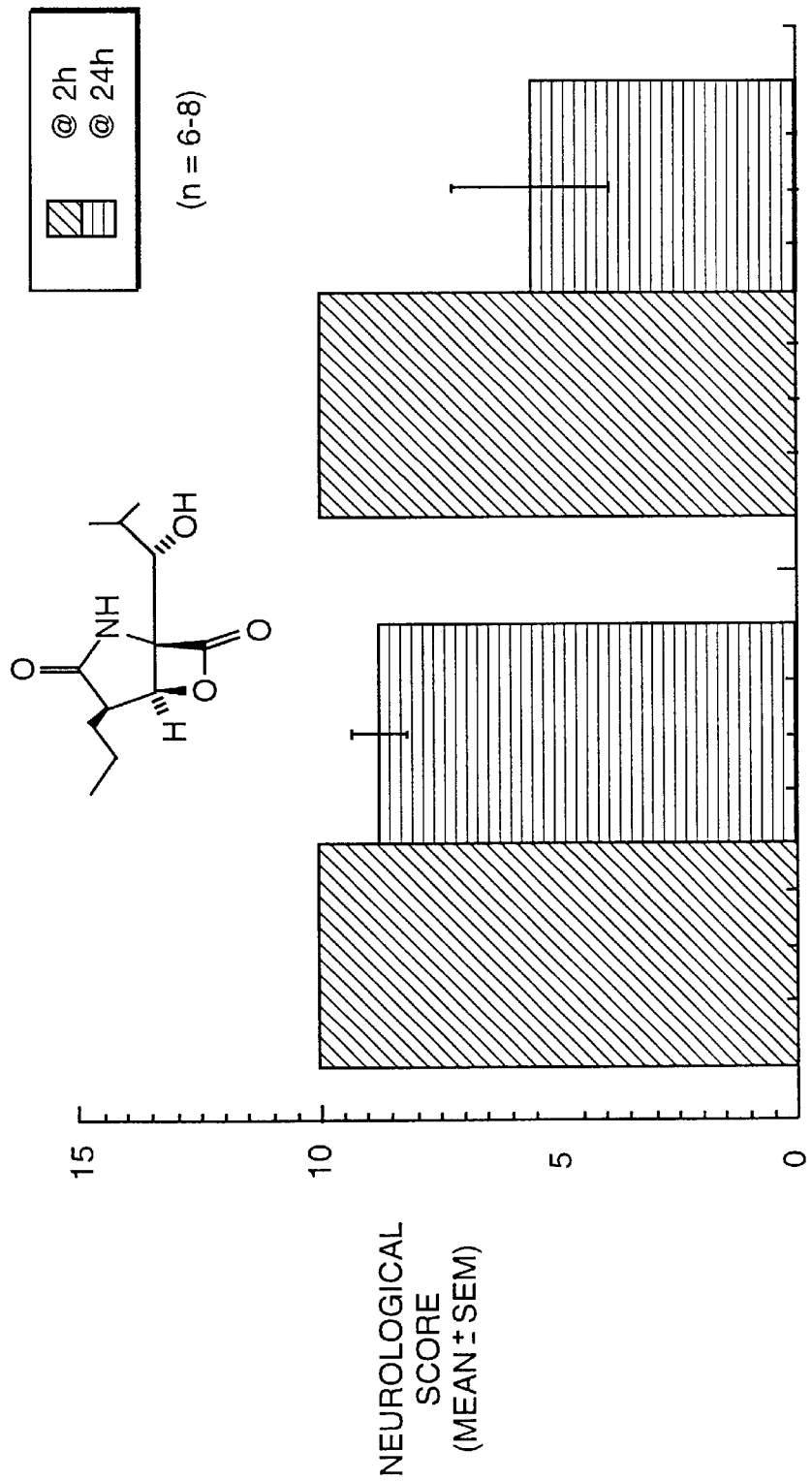
FIG. 6 is directed to reduction of neurological score by administration of the proteasome inhibitor 7-n-propyl-clasto-lactacystin β-lactone following middle cerebral artery (MCA) occlusion.

All animals had a neurological score of 10±0 immediately after the 2 hour ischemic episode. At 24 hours, the vehicle-treated rats had a mean score of 8.7±0.6, whereas rats treated with a single 0.1 mg/kg dose of 7-n-propyl-clasto-lactacystin β-lactone had a mean score of 5.5±1 (FIG. 6). These data represent a 40% neurological improvement for the drug-treated animals.

Conclusion 7-n-propyl-clasto-lactacystin β-lactone provides significant protection in both the degree of neurological deficit and infarcted brain damage.

Example 3

Methods

Male Sprague Dawley rats (250–400 g) were anesthetized with haloethane and subjected to middle cerebral artery (MCA) occlusion using a nylon filament for 2 h. Subsequently, the filament was removed and reperfusion of the infarcted tissue occurred for 24 hours before the rat was sacrificed.

Immediately after the filament was withdrawn, the animals were evaluated using a neurological scoring system. Neurological scores were expressed on a scale from 0 to 10, with 0 representing no neurological deficit and 10 representing severe neurological deficit. After 24 hours and before sacrifice, animals were evaluated a second time using the same neurological scoring system.

Staining of coronal sections (2.0 mm×7–8) with triphenyltetrazolium chloride (TTC) taken throughout the brain were evaluated under blinded conditions using image analysis to determine infarct size.

Dosing Regimen

Rats were given iv bolus injections (1.0 mL/kg) of either vehicle (50% propylene glycol/saline; n=8) or 7-n-propyl-clasto-lactacystin β-lactone (0.3 mg/kg; n=7) at 2 hours after the start of the occlusion. Two additional groups of rats were given iv bolus injections (1.0 mL/kg) of 7-n-propyl-clasto-lactacystin β-lactone at 0 minutes, 2 hours, and 6 hours after the start of the occlusion. One group (0.1 mg/kg×3; n=6) received 0.1 mg/kg at each of these times, while another group (0.3 mg/kg×3; n=7) received 0.3 mg/kg at each of the three timepoints.

Results

Figure 3:
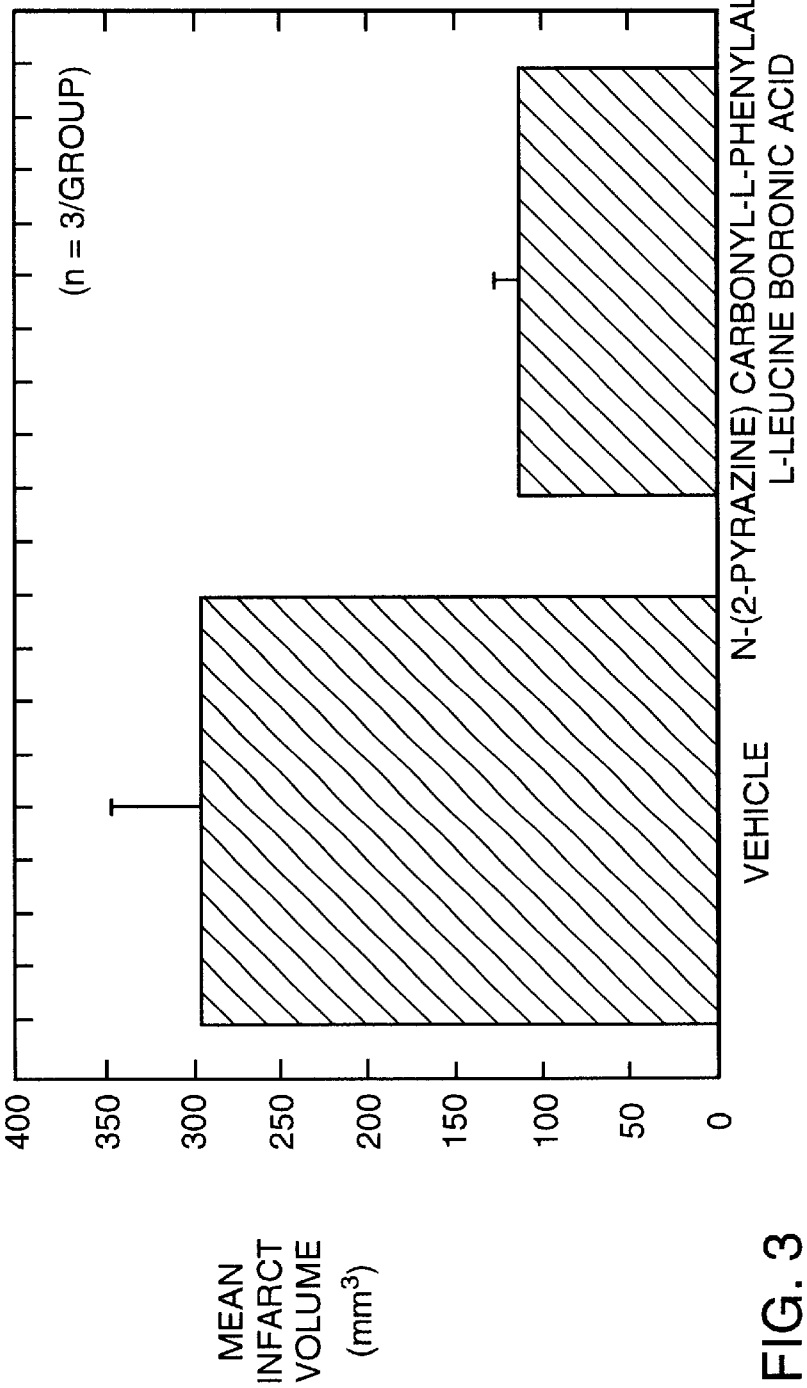
FIG. 3 is directed to reduction of infarct volume following middle cerebral artery (MCA) occlusion by administration of the proteasome inhibitor N-(2-pyrazine)carbonyl-L-phenylalanine-L-leucine boronic acid.
Figure 4:
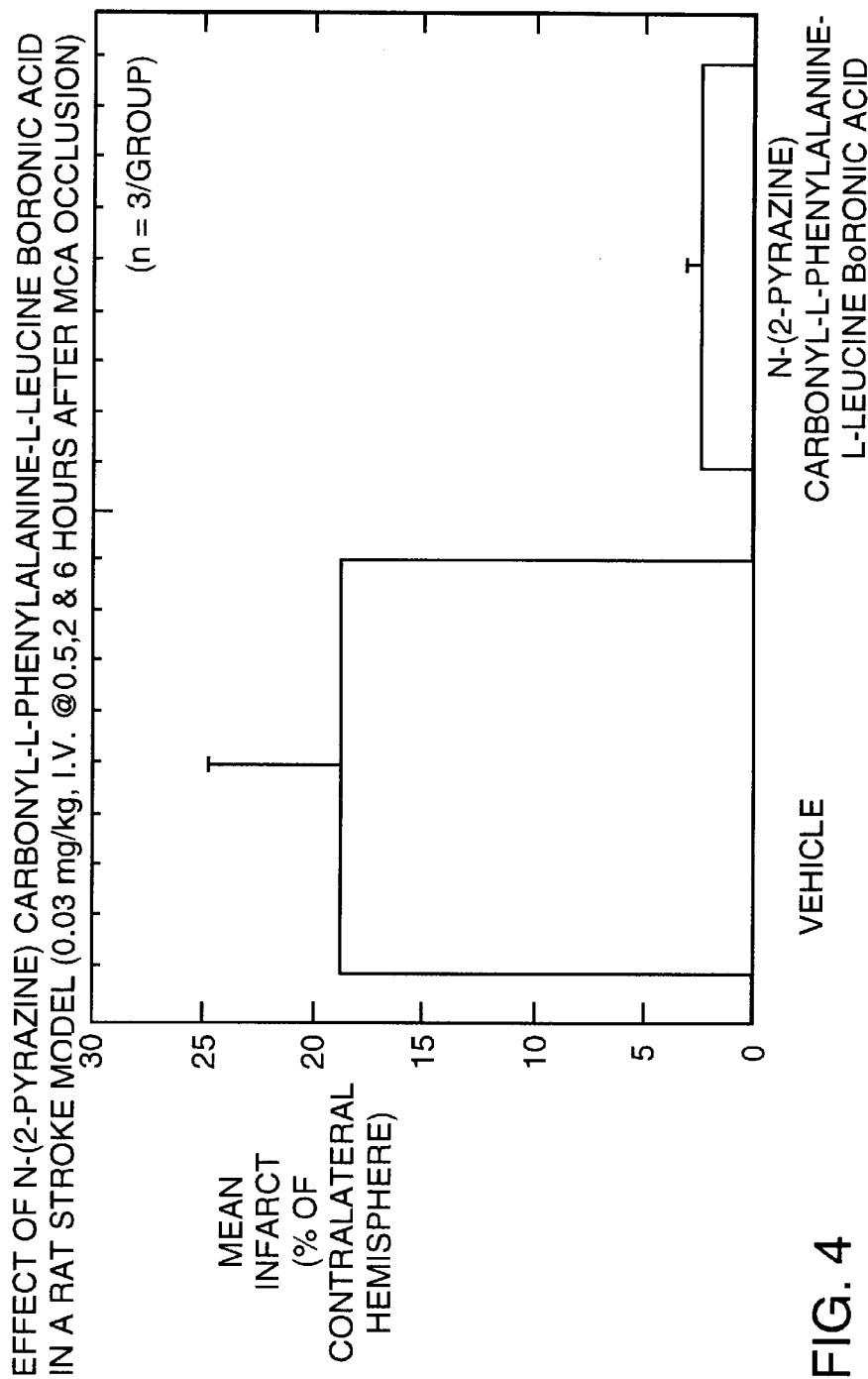
FIG. 4 is directed to reduction of infarct size, expressed as a percentage of the contralateral hemisphere, by administration of the proteasome inhibitor N-(2-pyrazine)carbonyl-L-phenylalanine-L-leucine boronic acid.

In animals treated with a single dose of 7-n-propyl-clasto-lactacystin β-lactone, infarct volume was decreased by 50% (FIG. 3). Infarct volume was not significantly decreased in either the 0.1 mg/kg×3 dosage group or the 0.3 mg/kg×3 dosage group (FIG. 7).

All animals had a neurological score of 10±0 immediately after the 2 hour ischemic episode. At 24 hours, the vehicle-treated rats had a mean score of 8.7±0.6, whereas rats treated with a single 0.3 mg/kg dose of 7-n-propyl-clasto-lactacystin β-lactone had a mean score of 4±1 (FIG. 8). These data represent a 60% neurological improvement for the drug-treated animals. No significant improvement in neurological score was observed in either the 0.1 mg/kg×3 dosage group or the 0.3 mg/kg×3 dosage group (FIG. 8).

Conclusion 7-n-propyl-clasto-lactacystin β-lactone provides significant protection in both the degree of neurological deficit and infarcted brain damage.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. A method of treating ischemic injury in a mammal comprising administering to said mammal an effective amount of an NF-κB activation inhibitor selected from the group consisting of proteasome inhibitors, ubiquitin pathway inhibitors, agents that interfere with the activation of NF-κB via the ubiquitin proteasome pathway, and mixtures thereof.

2. A method of treating reperfusion injury after ischemia in a mammal comprising administering to said mammal an effective amount of an NF-κB activation inhibitor selected from the group consisting of proteasome inhibitors, ubiquitin pathway inhibitors, agents that interfere with the activation of NF-κB via the ubiquitin proteasome pathway, and mixtures thereof.

3. A method of preventing, reducing the size or lessening the severity of infarct resulting from ischemia or reperfusion injury in a mammal comprising administering to said mammal an effective amount of an NF-κB activation inhibitor selected from the group consisting of proteasome inhibitors, ubiquitin pathway inhibitors, agents that interfere with the activation of NF-κB via the ubiquitin proteasome pathway, and mixtures thereof.

4. The method of any one of claims 1–3, wherein the ischemia is the result of vascular occlusion.

5. The method of claim 4 wherein the occlusion is of a cerebral vessel.

6. The method of claim 4 wherein the occlusion is of a cardiac vessel.

7. The method of any one of claims 1–3, wherein the method prevents or lessens the severity of stroke.

8. The method of any one of claims 1–3, wherein the method prevents or lessens the severity of stroke resulting from the occlusion of the cerebral vessel.

9. The method of claim 6 wherein the method prevents or lessens the severity of myocardial infarction resulting from the occlusion of a cardiac vessel.

10. The method of any one of claims 1–3, wherein the NF-κB activation inhibitor is an agent that inhibits phosphorylation of IκB-α.

11. The method of any one of claims 1–3, wherein the NF-κB activation inhibitor comprises a proteasome inhibitor.

12. The method of claim 11 wherein said proteasome inhibitor is a peptidyl aldehyde.

13. The method of claim 11 wherein said proteasome inhibitor is a peptidyl boronic acid or peptidyl boronic ester.

14. The method of claim 11 wherein said proteasome inhibitor is a lactacystin analog.

15. The method of claim 13 wherein said proteasome inhibitor is N-(2-pyrazine) carbonyl-L-phenylalanine-L-leucine boronic acid.

16. The method of claim 14 wherein the proteasome inhibitor is 7-n-propyl-clasto-lactacystin β-lactone.

17. The method of any one of claims 1–3, wherein the NF-κB activation inhibitor is administered to the mammal less than 12 hours after the onset of ischemia.

18. The method of any one of claims 1–3, wherein the NF-κB activation inhibitor is administered to the mammal less than 6 hours after the onset of ischemia.

19. The method of any one of claims 1–3, wherein the NF-κB activation inhibitor is administered to the mammal before the onset of ischemia.

20. The method of any one of claims 1–3, further comprising the step of administering a second agent.

21. The method of claim 20 wherein the second agent is selected from the group consisting of NF-κB activation inhibitors, agents which the expression or action of proinflammatory cytokines or cellular adhesion molecules, agents which are to reperfuse or oxygenate tissues, and agents which assist in temperature normalization.

22. The method of claim 20 wherein the second agent is selected from the group consisting of steroids, antiedema drugs, thrombolytics, clot solubilizing drugs, polyanions and anticoagulants.

23. The method of claim 22 wherein the second agent comprises a thrombolytic or clot solubilizing drug.

24. The method of claim 23 wherein the thrombolytic clot solubilizing drug comprises tissue plasminogen activator.

* * * * *

UNITED STATES PATENT AND TRADEMARK OFFICE
CERTIFICATE OF CORRECTION

PATENT NO. : 6,271,199 B2
DATED : August 7, 2001
INVENTOR(S) : Stephen J. Brand, Alfred L. Goldberg, Louis Plamondon, Francois Soucy, and Peter J. Elliott It is certified that error appears in the above-identified patent and that said Letters Patent is hereby corrected as shown below:

<u>Title page,</u>
Item [22] "Nov. 24, 1998" should be -- Feb. 17, 1998 --.

Signed and Sealed this

Nineteenth Day of March, 2002

Attest:

Attesting Officer

JAMES E. ROGAN
Director of the United States Patent and Trademark Office